United States Patent [19]

Zak

[11] 4,085,151
[45] Apr. 18, 1978

[54] BUTYNEDIOL PRODUCTION

[75] Inventor: Dennis Joseph Zak, Houston, Tex.

[73] Assignee: E. I. Du Pont de Nemours and Company, Wilmington, Del.

[21] Appl. No.: 811,283

[22] Filed: Jun. 29, 1977

[51] Int. Cl.² ............................................. C07C 29/00
[52] U.S. Cl. ................................................. 260/635 Y
[58] Field of Search ................................... 260/635 Y

[56] References Cited

U.S. PATENT DOCUMENTS

| | | | |
|---|---|---|---|
| 3,560,576 | 2/1971 | Kirchner | 260/635 Y |
| 3,650,985 | 3/1972 | Kirchner | 252/431 |
| 3,723,545 | 3/1973 | Nagel et al. | 260/635 Y |

FOREIGN PATENT DOCUMENTS

| | | | |
|---|---|---|---|
| 698,019 | 10/1953 | United Kingdom | 260/635 Y |
| 807,581 | 1/1959 | United Kingdom | 260/635 Y |
| 818,314 | 8/1959 | United Kingdom | 260/635 Y |

Primary Examiner—Joseph E. Evans

[57] ABSTRACT

The process for the production of butynediol by reacting acetylene and formaldehyde in the presence of a particulate copper acetylide catalyst at temperatures from 60° to 120° C is buffered to a pH of 5.0 to 8.0 by a mixture of sodium carbonate and sodium bicarbonate. The buffer mixture is obtained by scrubbing the recycle gas stream from the reaction with an aqueous solution of sodium carbonate and optionally sodium bicarbonate in a countercurrent absorption tower. The liquid effluent from the tower is split, with a portion going to the reaction as the buffer and the balance being regenerated with sodium hydroxide and recycled to the tower.

3 Claims, 1 Drawing Figure

U.S. Patent
April 18, 1978
4,085,151
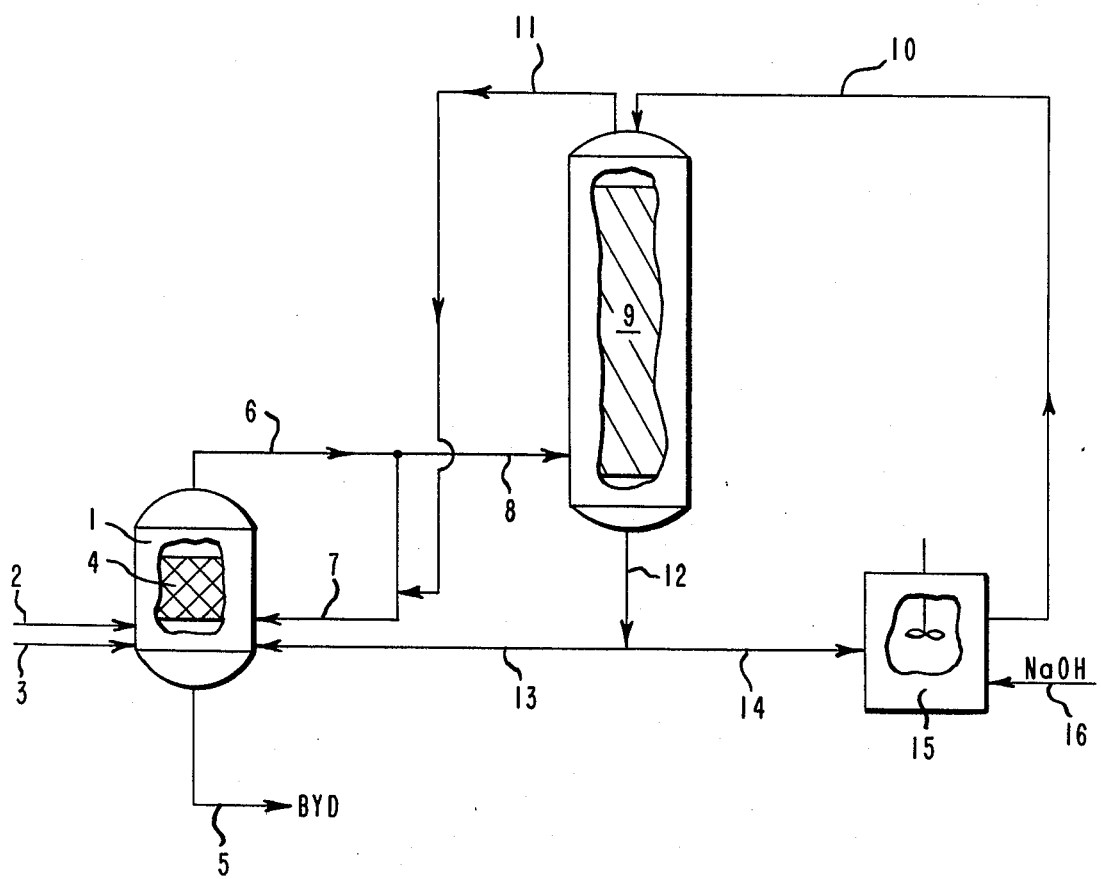

BUTYNEDIOL PRODUCTION

BACKGROUND OF THE INVENTION

1. Field of the Invention

This invention relates to an improved process for the preparation of butynediol by the reaction of acetylene and formaldehyde. More specifically, this invention relates to an improved process for the preparation of butynediol by the reaction of acetylene and formaldehyde in the liquid phase in the presence of an insoluble particular copper complex catalyst and a sodium carbonate-sodium bicarbonate buffer.

2. Description of the Prior Art

The preparation of butynediol by the reaction of formaldehyde and acetylene in the presence of a slurry of copper acetylide catalyst is described in British Pat. No. 698,019 and U.S. Pat. Nos. 2,939,844 and 3,154,589. An improved catalyst and process for the production of butynediol is described by Kirchner is U.S. Pat. Nos. 3,650,985 and 3,560,576. In the Kirchner patents it is disclosed that the pH of the reaction mixture during the ethynylation reaction may be maintained by ion exchange or acid acceptor treatment of the feed. Calcium carbonate is disclosed as an acid acceptor. Sodium carbonate and sodium bicarbonate have also been used for controlling pH during the ethynylation reaction.

At 90° to 100° C formaldehyde tends to disproportionate to methanol and formic acid. The presence of calcium results in the formation of calcium formate. Calcium formate, in the subsequent processing of crude filtrate from the butynediol reactor involving the stripping of formaldehyde and the hydrogenation of the residue directly over an activated nickel aluminum alloy catalyst to form an aqueous solution of butanediol, decomposes to insoluble calcium salts which foul heat exchanger surfaces and produces deposits on the hydrogenation catalyst causing a loss in activity.

Because of the above problem it has been customary to employ sodium bicarbonate to control the pH in such reactions. A major disadvantage of the bicarbonate salt is the generation of carbon dioxide which dilutes the recycle acetylene. A substantial purge of the recycle gas is required to maintain acetylene concentration, which results in substantial acetylene losses.

SUMMARY OF THE INVENTION

It has now been discovered that the preparation of butynediol by a process comprising contacting acetylene and formaldehyde in a reactor in the presence of a copper acetylide catalyst in an agitated aqueous medium in a continuous reaction at about 60° to 120° C, and a pH of 5.0 to 8.0, is improved by treating the gaseous overhead from the reactor in an absorption tower prior to recycling it to the reactor. The gaseous overhead, i.e., mainly acetylene, carbon dioxide and nitrogen, is fed into, and near the bottom of, a countercurrent absorption tower. In the tower the gas is contacted with a falling, aqueous solution of sodium carbonate or a mixture of sodium carbonate and sodium bicarbonate. The contact with the aqueous solution is controlled to remove part of the carbon dioxide present in the gaseous overhead, e.g., from 10 to 50% by volume, preferably 10 to 15%, by converting it to sodium bicarbonate. The amount removed will be such to keep the carbon dioxide level in the reactor below 3% by volume. In a preferred embodiment the amount of carbon dioxide removed will equal that generated in the reactor. The gaseous overhead is then recycled to the reactor. The bottoms of the tower, i.e., the aqueous solution of sodium carbonate and sodium bicarbonate is removed and divided into two parts. One part is fed into the reactor in an amount sufficient to buffer the reaction mass to the desired pH range, i.e., pH 5.0 to 8.0, preferably pH 6.0 to 6.5. The remainder of the solution is then contacted with sodium hydroxide in a suitable vessel. The amount of sodium hydroxide added should be sufficient to convert the sodium bicarbonate formed from carbon dioxide into sodium carbonate. The stream is then recycled to the absorption tower.

The advantage of the above process is that the desired pH control of the butynediol reaction can be obtained without the need to purge significant amounts of carbon dioxide and acetylene from the gaseous recycle stream.

It should be noted that it is not necessary to feed all of the gaseous overhead into the absorption tower. In most instances it will be desirable to treat 30 to 50 percent by volume of this stream, preferably 35 to 40%. The remainder can be recycled directly to the reactor as the total concentration of carbon dioxide within the reactor will not be sufficient to affect the activity of the catalyst.

The gaseous overhead from the reactor need not be fed directly into absorption tower. The overhead may first be fed into a compressor where the pressure will be increased so that it can flow through the packed column of the absorption tower. In another embodiment the overhead can be combined with the acetylene fed to the reactor and all or part of the combined stream fed to the absorption tower to remove sufficient carbon dioxide to obtain the desired level in the reactor, i.e., less than 3% by volume.

DESCRIPTION OF THE DRAWING

The FIGURE is a process flow diagram of an embodiment of the process of the invention.

DESCRIPTION OF THE INVENTION

In the ethynylation process of this invention formaldehyde and acetylene are contacted in the presence of a copper acetylide catalyst is an agitated aqueous medium in a continuous reaction. The catalyst may be in a fixed bed or a slurry of particulate catalyst in an aqueous medium. Preferably the catalyst is in the form of a slurry since backmixing which provides more homogeneous control of pH is readily achieved in this manner. In a slurrry catalyst system the formaldehyde and acetylene are continuously fed into, and preferably below the surface of, the aqueous catalyst slurry in the reaction zone, and thoroughly mixed with the catalyst slurry by mechanical stirring, gas agitation, sonic waves or other means. The effluent is continuously withdrawn from the reaction zone, such as through filter elements immersed in the agitated catalyst slurry which separate the catalyst from the liquid effluent.

The amount of catalyst used in the ethynylation process is not critical, but is preferably such as to provide about 0.1 to 10% by weight of copper based of the total liquid medium. The reaction temperature is desirably maintained at about 60° to 120° C, and preferably about 80° to 115° C.

The formaldehyde concentration in the liquid medium in contact with the slurried catalyst during the course of the ethynylation reaction will be ordinarily about 1 to 20, and preferably about 5 to 15, weight percent under steady state conditions. The acetylene partial pressure may vary from subatmospheric to elevated pressures of about 20 atmospheres or higher. Preferably, the acetylene partial pressure is in the range of about 0.001 to 2 atmospheres. Advantageously, the acetylene partial pressure will be in the range of about 0.005 to 0.5 atmosphere per weight part of formaldehyde present in 100 parts of said medium, and preferably about 0.01 to 0.3 atmosphere per weight part of formaldehyde present in 100 parts of said medium. In the substantial absence of extraneous gas, the acetylene partial pressure may be taken as the absolute pressure less the vapor pressure of water at the reaction temperature. Crude acetylene may be used, but for safety reasons it should be substantially free of oxygen.

The liquid effluent from the ethynylation reactor is heated to volatilize formaldehyde, propargyl alcohol and a portion of the water present. These volatile components are then condensed and combined with supplemental concentrated formaldehyde for recycle to the ethynylation reactor while purging any buildup of methanol at convenient intervals. The balance of the effluent is recovered as aqueous butynediol. It is in the calandria of this recycle unit that the process of the invention eliminates a fouling problem that could occur when calcium carbonate is employed. Alternatively, effluent from the continuous ethynylation reaction may be fed to a conventional plug flow ethynylation to react any excess formaldehyde. The rate of feeding formaldehyde will then ordinarily result in at least about 50%, and preferably about 75 to 85%, formaldehyde conversion across the reaction zone.

The catalyst used in the ethynylation reaction may be any copper acetylide. It may be supported or unsupported. Suitable supports include silica gel and activated carbon. The catalyst may be prepared by passing acetylene over a suitable copper compound such as cupric or cuprous chloride or the catalyst may be prepared in situ during the ethynylation reaction.

The preferred ethynylation catalysts used in the process of this invention are the particulate catalysts described by Kirchner in U.S. Pat. No. 3,650,985. These catalysts are especially reactive cuprous acetylide complexes which must be prepared in a particular manner. These catalysts are prepared by a topochemical reaction of formaldehyde, acetylene and particles of water-insoluble cupric compound slurried in an aqueous medium. The topochemical reaction continues until particulate complexes are obtained in which the cupric compound is substantially completely converted to cuprous acetylide. Illustrative of suitable insoluble cupric compounds are cupric oxide, cupric silicate, cupric phosphate, cupric hydroxide, basic cupric carbonate and the like. Of these, the basic cupric carbonates are particularly preferred because of the rapidity with which active catalysts can be prepared from them and because of the superlative filterability, purity, stability and activity of the resulting catalysts.

Some control of the total surface area and particle size of these preferred catalysts can be achieved by control of the size and distribution of particle sizes of the precursor particles. The particles tend to grow in cross-section as the conversion to acetylide proceeds. Preferably, the precursor particles will be substantially all larger than about 2.0 microns in cross-sectional dimension, as determined by Coulter Counter analysis, and will have a total surface area of at least about 5.0 square meters per gram as determined by nitrogen absorption.

In preparing the preferred particulate complexes, the slurried cupric precursor is subjected to the simultaneous action of formaldehyde and acetylene at a partial pressure of not more than about 2.0 atmospheres in a substantially neutral aqueous medium at about 50° to 120° C. Preferably, the catalyst preparation temperature is in the range of about 65° to 80° C. The pH of the aqueous medium is in the range of about 5.0 to 8.0, and preferably about 6.0 to 7.0, at the outset of the reaction. The concentration of formaldehyde in the aqueous medium is ordinarily in the range of about 1.0 to 66.0, advantageously at least about 5.0, and preferably about 20 to 40 weight percent, at the outset of the reaction. Ordinarily, the amount of liquid medium will be such as to provide about 5 to 20 moles of formaldehyde per gram atom of cupric copper in the precursor. Ordinarily, the partial pressure of acetylene over the aqueous medium is in the range of about 0.005 to 0.5 atmosphere per weight part of formaldehyde present in 100 parts of the aqueous liquid medium, and preferably about 0.01 to 0.3 atmosphere per weight part of formaldehyde present in 100 parts of the aqueous liquid medium.

The preferred particulate ethynylation catalysts prepared in the manner described above consist essentially of a cuprous acetylide complex containing at least about 1.75 carbon atoms per copper atom, as determined by combustion analysis, having a total surface area of at least about 5.0 square meters per gram, and in which at least about 75 weight percent of the particle have a cross-sectional dimension of at least 5.0 microns. In the most preferred embodiment of the invention, the catalyst consists entirely of the specified cuprous acetylide complex. However, the preferred catalyst may also contain other materials, e.g., supports such as carbon or silica, cuprene inhibitors such as carbon or silica, cuprene inhibitors such as bismuth oxide, other copper acetylide complexes, unconverted catalyst precursors or residues therefrom, and the like, if desired, in amounts which do not noticeably detract from the filter-ability and activity of the catalyst.

The phrase "carbon atoms per copper atom, as determined by combustion analysis" defines the number of carbon atoms per copper atom, as determined by combustion analysis of the catalyst, after filtering, water washing, air drying, and final drying over anhydrous calcium sulfate for three days, and correcting for the weight of any components present other than copper acetylide complexes. The atomic ratio of carbon to copper, so determined, is ordinarily about 2.0 to 12.5, and preferably about 2.5 to 5.0.

The preferred cuprous acetylide complex catalysts have a total surface area of at least about 5.0, and commonly about 5.0 to 75.0 square meters per gram, as determined by nitrogen absorption measurement on the particles after separating and drying as specified for combustion analysis. Preferably, the catalyst has a total surface area of at least about 15 square meters per gram. The preferred catalysts are further characterized in that at least about 75, and usually at least about 85, or more, weight percent of the catalyst is in the form of particles having a cross-sectional dimension of at least 5 microns, ordinarily 5 to 40 microns, and preferably 8 to 30 microns, as determined by Coutler Counter analysis. The size of the average particle is preferably about 10 to 20 microns for optimum combination of filterability and activity. In particularly preferred catalysts substantially all of the particles are larger than about 3 microns in at least one cross-sectional dimension.

The gaseous overhead from the reactor usually consists of 25 to 40% by volume acetylene, 1 to 3% carbon dioxide, 40 to 50% water, 4 to 7% methanol, 4 to 7% formaldehyde and 3 to 6% inerts or other compounds, e.g., nitrogen propargyl alcohol, butynediol, methyl acetylene, methyl propargyl alcohol, etc. The carbon dioxide content of this stream must be reduced by removing the amount produced in the reactor before the stream is recycled to the reactor, otherwise the catalyst could be damaged.

Rather than a purge of this carbon dioxide and at the same time a purge of valuable acetylene, part of the stream is fed into an absorbing tower. If the gaseous overhead is fed directly into the absorbing tower, normally 35 to 40% by volume of the stream will be fed into the tower and the remainder recycled directly to the reactor. The important parameter is that the carbon dioxide content of the reactor should be kept below 3% by volume to avoid damage to the catalyst.

The gas will enter the tower near the bottom and flow upward countercurrent to a liquid scrubbing stream. The tower will normally be a packed column. Although preferred, this is not critical and other type columns can be employed, for example, bubble cap or sieve tray.

The scrubbing stream will be an aqueous solution of sodium carbonate or a mixture of sodium carbonate and sodium bicarbonate. The pH of the scrubbing solution is determined by the total sodium normally and the ratio of sodium carbonate to sodium bicarbonate. As part of the solution will be used to buffer the reaction to the pH 5.0 to 8.0 level, these parameters should be controlled to obtain the desired pH. In order to avoid solubility and crystallization problems, the solution will usually not exceed 2N in sodium. In a prefered embodiment the stream is approximately 1N in sodium with about 50% by weight as carbonate and 50% as bicarbonate.

Within the tower the sodium carbonate will react with the carbon dioxide and water to form sodium bicarbonate. In this manner the carbon dioxide is removed from the recycle stream, and the stream can then be recycled to the reactor.

The temperature of the scrubbing step can vary over a range of 45° to 60° C, preferably about 50° to 55° C, as the absorption coefficient increases with increasing temperatures.

The pressure of the scrubbing step can range from 15 to 30 psia. Preferably the pressure will be 16 to 20 psia or at about the same pressure as the overhead has when it leaves the reactor. In some embodiments it will be necessary to compress the treated gas stream before it is recycled to the reactor, i.e., to compensate for the pressure drop through the absorption tower.

Since the mass transfer coefficient increases with increasing liquid rate, the liquid flow rate should vary from 8 to 15 times the gas rate, preferably 10 times.

A minor portion, 0.5 to 5% by weight, of the spent scrubbing solution will be fed into the reactor as the buffer solution. The amount so fed should be sufficient to maintain the reaction within the desired pH range, i.e., pH 5.0 to 8.0, preferably pH 6.0 to 6.5.

The remainder of the scrubbing solution will be fed to a suitable mixing tank where sodium hydroxide will be added to convert the sodium bicarbonate created from carbon dioxide in the tower into sodium carbonate. The stream will then be recycled to the top of the tower.

An embodiment of the process of the invention will now be explained with reference to the FIGURE.

Into a reactor 1 is fed acetylene 2 and formaldehyde 3. The feedstocks react in the presence of a copper acetylide catalyst 4 to produce butynediol (BYD). The BYD is removed from the bottom of the reactor through line 5 and can be further reacted to produce butanediol (not illustrated).

The gaseous overhead 6 from the reactor contains unreacted acetylene, carbon dioxide and other gases. This overhead is split into two portions. One portion is recycled into the reactor through line 7. The other portion 8 is fed into, and near the bottom of, an absorption tower 9, illustrated as a packed column.

Within the tower the gas is contacted counter-current with an aqueous solution of sodium carbonate or a sodium carbonate-sodium bicarbonate mixture. This solution is fed into the tower through line 10. The scrubbing solution removed some of the carbon dioxide present in the gas; and the cleaned gas is recycled to the reactor through line 11.

The scrubbing solution collects in the bottom of the tower and is removed through line 12. A portion of the solution is fed into the reactor through line 13 to maintain the desired reaction pH. The remainder is fed through line 14 to a mixer 15 where it is mixed to sodium hydroxide 16. The addition of sodium hydroxide converts part or all of the sodium bicarbonate present into sodium carbonate. The sodium carbonate or sodium carbonate-sodium bicarbonate mixture is then fed into the tower through line 10 as previously explained.

I claim:

1. In the process for the production of butynediol by reacting acetylene and formaldehyde in a reactor in the presence of a particulate copper acetylide catalyst in an agitated aqueous medium at 60° to 120° C and at a pH of 5.0 to 8.0, where the gaseous overhead from the reactor is recycled to the reactor, the improvement comprising feeding at least part of the gaseous overhead into a countercurrent absorption tower wherein it is contacted with an aqueous solution of sodium carbonate or a mixture of sodium carbonate and sodium bicarbonate to remove the carbon dioxide produced in the reactor, the gas stream then being recycled to the reactor, and the liquid bottoms from the absorption tower containing sodium carbonate and sodium bicarbonate being split into two parts, one part being fed into the reactor in an amount sufficient to maintain the pH of 5.0 to 8.0 and the remainder being contacted with sufficient sodium hydroxide to convert the sodium bicarbonate created by absorption of the carbon dioxide into sodium carbonate, and recycling the converted stream to the absorption tower.

2. The process of claim 1 in which the pH is in the range of 6.0 to 6.5.

3. The process of claim 1 wherein the gaseous overhead is combined with the acetylene fed to the reactor and then fed into the absorption tower.

* * * * *